(12) United States Patent
Rajagopal

(10) Patent No.: US 12,121,775 B2
(45) Date of Patent: Oct. 22, 2024

(54) BRACE FOR PREVENTING FINGER INJURIES

(71) Applicant: Dhiren Rajagopal, Atlanta, GA (US)

(72) Inventor: Dhiren Rajagopal, Atlanta, GA (US)

( * ) Notice: Subject to any disclaimer, the term of this patent is extended or adjusted under 35 U.S.C. 154(b) by 190 days.

(21) Appl. No.: 16/019,538

(22) Filed: Jun. 27, 2018

(65) Prior Publication Data
US 2020/0001135 A1    Jan. 2, 2020

(51) Int. Cl.
*A63B 29/08*    (2006.01)
*A61F 5/01*    (2006.01)

(52) U.S. Cl.
CPC ............ *A63B 29/08* (2013.01); *A61F 5/0118* (2013.01)

(58) Field of Classification Search
CPC ........ A61F 13/104; A61F 13/105; A61F 5/01; A61F 5/013; A61F 5/05866; A61F 5/05875; A61F 5/0118; A61F 5/04; A61F 5/10; A61F 5/50; A61F 2/586; A61F 2002/587; A61F 2/54; A61F 2/58; A61H 1/02
USPC ....... 602/5, 12, 15, 21, 22; 128/880; 623/59, 623/60, 62, 63, 54, 65; 482/47, 48
See application file for complete search history.

(56) References Cited

U.S. PATENT DOCUMENTS

| | | | | |
|---|---|---|---|---|
| 1,733,933 A | * | 10/1929 | Beltz .................... | A61F 5/50 128/880 |
| 4,220,334 A | * | 9/1980 | Kanamoto ............. | A63B 23/16 601/40 |
| 4,242,715 A | | 12/1980 | Laird | |
| 4,337,496 A | | 6/1982 | Laird | |
| 4,441,489 A | * | 4/1984 | Evans ................. | A61F 5/05875 602/22 |

(Continued)

FOREIGN PATENT DOCUMENTS

| | | |
|---|---|---|
| AU | 2016202264 A1 | 11/2016 |
| AU | 2018248292 B2 | 10/2019 |

(Continued)

OTHER PUBLICATIONS

LMB (Spring-Coil Finger Extension Splint Capener or Wynn Perry, Amazon.com, https://www.amazon.com/LMB-Spring-Coil-Finger-Extension-Splint/dp/B07VSHYBQF, Jun. 2, 2009) (Year: 2009).*

(Continued)

*Primary Examiner* — Ophelia A Hawthorne
*Assistant Examiner* — Michael Milo
(74) *Attorney, Agent, or Firm* — FisherBroyles LLP

(57) ABSTRACT

A brace for preventing injuries to annular pulley ligaments in fingers of human hands includes a proximal band dimensioned to be worn on a proximal phalanx of a finger, a distal band dimensioned to be worn on a middle phalanx, and a coupling attached to the bands. The band may be worn in position overlying an annular pulley ligament of the fingers. The coupling may bias the bands away from each other to promote retention over the annular pulley ligaments. The coupling may limit movement of bands (and thus finger) to a predetermined range of motion for avoiding tearing of the annular pulley ligament. The coupling may provide a mechanical stop limiting movement to positions in which annular pulley injuries are less likely. The coupling may be provided as a gas-pressurized struts or compressible coil springs, which may be mounted to the bands in diametrically opposed positions.

19 Claims, 3 Drawing Sheets

(56) References Cited

U.S. PATENT DOCUMENTS

| | | | |
|---|---|---|---|
| 4,657,000 A * | 4/1987 | Hepburn | A61F 5/0102 602/16 |
| 4,665,905 A * | 5/1987 | Brown | A61F 5/0118 602/16 |
| 4,677,971 A * | 7/1987 | Lindemann | A61F 5/0118 473/62 |
| 4,746,057 A | 5/1988 | Wagner | |
| 4,830,360 A | 5/1989 | Carr, Jr. | |
| 5,020,524 A * | 6/1991 | Donohue | A61F 5/0118 602/22 |
| 5,038,764 A * | 8/1991 | Paez | A61F 5/0118 602/22 |
| 5,079,776 A | 1/1992 | Crawford | |
| 5,230,699 A * | 7/1993 | Grasinger | A61F 5/05866 128/880 |
| 5,569,306 A | 10/1996 | Thal | |
| 5,662,704 A | 9/1997 | Gross | |
| 5,706,520 A | 1/1998 | Thornton | |
| 5,849,004 A | 12/1998 | Bramlet | |
| 6,042,583 A | 3/2000 | Thompson | |
| 6,093,162 A | 7/2000 | Fairleigh | |
| 7,431,725 B2 | 10/2008 | Stack | |
| 8,236,049 B2 | 8/2012 | Rowe et al. | |
| 8,273,973 B2 | 9/2012 | Kimmons | |
| 8,333,155 B2 | 12/2012 | Cylvick | |
| 8,403,938 B2 | 3/2013 | Aeschlimann | |
| 8,449,599 B2 | 5/2013 | Chau et al. | |
| 8,489,165 B2 | 7/2013 | Segman | |
| 8,549,175 B2 | 10/2013 | Krishna | |
| 8,579,964 B2 | 11/2013 | Lane | |
| 8,728,155 B2 | 5/2014 | Montorfano et al. | |
| 8,858,623 B2 | 10/2014 | Miller | |
| 8,932,348 B2 | 1/2015 | Solem et al. | |
| 8,998,976 B2 | 4/2015 | Gregg et al. | |
| 9,005,084 B2 | 4/2015 | Silagy | |
| 9,033,383 B2 | 5/2015 | Rampersad | |
| 9,034,033 B2 | 5/2015 | McLean et al. | |
| 9,078,749 B2 | 7/2015 | Lutter et al. | |
| 9,375,312 B2 | 6/2016 | Weber | |
| 9,402,720 B2 | 8/2016 | Richter et al. | |
| 9,439,763 B2 | 9/2016 | Geist et al. | |
| 9,441,832 B2 | 9/2016 | Bushee | |
| 9,474,605 B2 | 10/2016 | Rowe et al. | |
| 9,578,982 B2 | 2/2017 | Rampersad | |
| 9,675,454 B2 | 6/2017 | Vidlund | |
| 9,849,001 B2 | 12/2017 | Thompson, Jr. | |
| 10,039,639 B2 | 8/2018 | Marchand et al. | |
| 10,420,645 B2 | 9/2019 | Del Nido | |
| 10,499,941 B2 | 12/2019 | Suri | |
| 10,639,168 B2 * | 5/2020 | Thompson, Jr. | A61F 2/586 |
| 10,820,991 B2 | 11/2020 | Rajagopal | |
| 10,820,992 B2 | 11/2020 | Rajagopal | |
| 11,103,351 B2 | 8/2021 | Rajagopal | |
| 11,123,187 B2 | 9/2021 | Rajagopal | |
| 2002/0013571 A1 | 1/2002 | Goldfarb | |
| 2004/0138707 A1 | 7/2004 | Greenhalgh | |
| 2004/0190383 A1 | 9/2004 | Marcucelli | |
| 2005/0075727 A1 | 4/2005 | Wheatley | |
| 2005/0137697 A1 | 6/2005 | Salahieh et al. | |
| 2005/0137698 A1 | 6/2005 | Salahieh | |
| 2006/0235509 A1 | 10/2006 | Lafontaine | |
| 2006/0241656 A1 | 10/2006 | Starksen et al. | |
| 2006/0241745 A1 | 10/2006 | Solem | |
| 2007/0049942 A1 | 3/2007 | Hindrichs et al. | |
| 2007/0118151 A1 | 5/2007 | Davidson | |
| 2007/0142838 A1 | 6/2007 | Jordan | |
| 2007/0277279 A1 | 12/2007 | Battat | |
| 2008/0125860 A1 | 5/2008 | Webler et al. | |
| 2008/0228165 A1 | 9/2008 | Spence | |
| 2009/0276040 A1 | 11/2009 | Rowe et al. | |
| 2010/0016655 A1 | 1/2010 | Annest et al. | |
| 2010/0094314 A1 | 4/2010 | Hernlund et al. | |
| 2011/0004296 A1 | 1/2011 | Lutter et al. | |
| 2011/0011917 A1 | 1/2011 | Loulmet | |
| 2011/0112737 A1 | 5/2011 | Neelakantan et al. | |
| 2011/0224785 A1 | 9/2011 | Hacohen | |
| 2011/0301698 A1 | 12/2011 | Miller et al. | |
| 2011/0312018 A1 | 12/2011 | Shusta et al. | |
| 2012/0078360 A1 | 3/2012 | Rafiee | |
| 2012/0136430 A1 | 5/2012 | Sochman et al. | |
| 2012/0289877 A1 * | 11/2012 | Hegland | A61F 5/013 602/22 |
| 2013/0023985 A1 | 1/2013 | Khairkhahan et al. | |
| 2013/0035757 A1 | 2/2013 | Zentgraf | |
| 2013/0079873 A1 | 3/2013 | Migliazza | |
| 2013/0116780 A1 | 5/2013 | Miller | |
| 2013/0172978 A1 | 7/2013 | Vidlund et al. | |
| 2013/0184811 A1 | 7/2013 | Rowe et al. | |
| 2013/0190861 A1 | 7/2013 | Chau et al. | |
| 2013/0211508 A1 | 8/2013 | Lane et al. | |
| 2013/0282059 A1 | 10/2013 | Ketai et al. | |
| 2013/0282110 A1 | 10/2013 | Schweich, Jr. et al. | |
| 2013/0304197 A1 | 11/2013 | Buchbinder et al. | |
| 2013/0331929 A1 | 12/2013 | Mitra et al. | |
| 2014/0005778 A1 | 1/2014 | Buchbinder et al. | |
| 2014/0031928 A1 | 1/2014 | Murphy et al. | |
| 2014/0163668 A1 | 6/2014 | Rafiee | |
| 2014/0296972 A1 | 10/2014 | Tegels et al. | |
| 2014/0316516 A1 | 10/2014 | Vidlund et al. | |
| 2014/0379076 A1 | 12/2014 | Vidlund et al. | |
| 2015/0025553 A1 | 1/2015 | Del Nido | |
| 2015/0142103 A1 | 5/2015 | Vidlund | |
| 2015/0313620 A1 | 5/2015 | Suri | |
| 2015/0196393 A1 | 7/2015 | Vidlund | |
| 2015/0223934 A1 | 8/2015 | Vidlund | |
| 2015/0250590 A1 | 9/2015 | Gries et al. | |
| 2015/0366556 A1 | 12/2015 | Khairkhahan et al. | |
| 2015/0366666 A1 | 12/2015 | Khairkhahan et al. | |
| 2016/0022501 A1 | 1/2016 | Schultz | |
| 2016/0120646 A1 | 5/2016 | Dwork et al. | |
| 2016/0213467 A1 | 7/2016 | Backus et al. | |
| 2016/0262878 A1 | 9/2016 | Backus et al. | |
| 2016/0262881 A1 | 9/2016 | Schankereli et al. | |
| 2016/0310268 A1 | 10/2016 | Oba et al. | |
| 2016/0317305 A1 | 11/2016 | Pelled et al. | |
| 2016/0324635 A1 | 11/2016 | Vidlund et al. | |
| 2016/0367360 A1 | 12/2016 | Cartledge et al. | |
| 2017/0143478 A1 | 5/2017 | Schwartz et al. | |
| 2017/0172737 A1 | 6/2017 | Kuetting et al. | |
| 2017/0209293 A1 | 7/2017 | Combs | |
| 2017/0227320 A1 | 8/2017 | Derousse | |
| 2017/0312078 A1 | 11/2017 | Krivoruchko | |
| 2017/0340443 A1 | 11/2017 | Stearns | |
| 2018/0085215 A1 | 3/2018 | Vaturi et al. | |
| 2018/0289473 A1 | 10/2018 | Rajagopal et al. | |
| 2018/0289474 A1 | 10/2018 | Rajagopal et al. | |
| 2018/0289485 A1 | 10/2018 | Rajagopal et al. | |
| 2018/0318071 A1 | 11/2018 | Lozonschi et al. | |
| 2019/0015205 A1 | 1/2019 | Rajagopal et al. | |
| 2020/0001135 A1 | 1/2020 | Rajagopal | |
| 2021/0000595 A1 | 1/2021 | Rajagopal | |
| 2021/0106422 A1 | 4/2021 | Rajagopal | |

FOREIGN PATENT DOCUMENTS

| | | |
|---|---|---|
| AU | 2018248410 B2 | 10/2019 |
| AU | 2020363981 A1 | 4/2022 |
| CA | 3059102 | 10/2018 |
| CA | 3059106 A1 | 10/2018 |
| CN | 102869318 A | 1/2013 |
| CN | 105744915 A | 7/2013 |
| CN | 103491901 A | 1/2014 |
| CN | 103826570 A | 5/2014 |
| CN | 103826750 A | 5/2014 |
| CN | 103889369 A | 6/2014 |
| CN | 106618798 A | 5/2017 |
| CN | 105658178 B | 5/2018 |
| DE | 10 2012 002 785 A1 | 8/2013 |
| DE | 102012002785 | 8/2013 |
| EP | 0503182 | 9/1992 |
| EP | 1462880 A2 | 9/2004 |
| EP | 1462880 A3 | 4/2005 |
| EP | 3 311 774 A1 | 4/2018 |

(56) References Cited

FOREIGN PATENT DOCUMENTS

| | | | |
|---|---|---|---|
| EP | 3606444 A4 | 2/2020 | |
| EP | 3954342 A1 * | 2/2022 | ............ A61F 5/0118 |
| JP | 2013-503009 A1 | 1/2013 | |
| JP | 2013540469 A1 | 11/2013 | |
| JP | 2014523256 A1 | 9/2014 | |
| KR | 20130027807 A * | 3/2013 | |
| KR | 10-2020-0007805 A | 1/2020 | |
| KR | 10-2020-0007806 A | 1/2020 | |
| UY | 37667 A | 10/2018 | |
| UY | 37668 A | 10/2018 | |
| WO | 1994/020049 A1 | 9/1994 | |
| WO | 9420049 | 9/1994 | |
| WO | 1994020049 | 9/1994 | |
| WO | WO-9420049 A1 * | 9/1994 | ............... A61F 5/04 |
| WO | 2005094711 A2 | 10/2005 | |
| WO | 2014/021905 A1 | 2/2014 | |
| WO | 2015/020682 A1 | 2/2015 | |
| WO | 2015200497 A1 | 12/2015 | |
| WO | 2016/050751 A1 | 4/2016 | |
| WO | 2016126739 | 8/2016 | |
| WO | 2016168609 A1 | 10/2016 | |
| WO | 2016/179427 A1 | 11/2016 | |
| WO | 2016/186909 A1 | 11/2016 | |
| WO | 20161794271 | 11/2016 | |
| WO | 098100 S | 6/2017 | |
| WO | DM/098 100 S | 6/2017 | |
| WO | 2017/117560 A1 | 7/2017 | |
| WO | 2017201196 A1 | 11/2017 | |
| WO | 2018/187390 A1 | 10/2018 | |
| WO | 2018187495 A1 | 10/2018 | |
| WO | 2020/005527 A1 | 1/2020 | |
| WO | 2021072193 A1 | 4/2021 | |

OTHER PUBLICATIONS

JamesSpring (Spring & Wire Co., Compression Spring Uses, https://www.jamesspring.com/news/what-are-compression-springs/, Mar. 9, 2015) (Year: 2015).*

Bunnell (74120 Modified Safety Pin Splint, Small, 2-1/2"; Jun. 2012; https://www.amazon.com/Built-Up-Stainless-Steel-Easy-Hold-Removable-Arthritis/dp/B07BFRD57Z?th=1) (Year: 2012).*

Mini Modified Safety Pin Splint with Coil to Extend PIP or DIP, Jun. 21, 2012; https://www.amazon.com/Bunnell-Modified-Safety-Splint-Extend/dp/B07BHXWV86/ref=sr_1_4?crid=3SD60L7E0ZW62&keywords=bunnell%2Bsplint%2Bfinger&qid=1687898663&s=industrial&sprefix=bunnell%2Bsplint%2Bfinger%2Cindustrial%2C (Year: 2012).*

International Search Report and Written Opinion of the International Searching Authority mailed Aug. 30, 2019, in International Application No. PCT/US19/36428.

Extended European Search Report mailed Feb. 28, 2022, in European Application No. 19825443.5.

European Search report issued for corresponding EP Application No. 18780758.1 on Apr. 30, 2021.

Supplementary European Search report issued for corresponding EP Application No. 18781785.3 on Mar. 19, 2021.

Bai, et al. An Integrated Pericardial Valved Stent Special for Percutaneous Tricuspid Implantation: An Animal Feasibility Study; Journal of Surgical Research 160, 215-221 (2010).

International Search Report and Written Opinion in corresponding International application No. PCT/PCT/US2021/042284 on Nov. 17, 2021.

Extended European Search Report mailed Oct. 25, 2022, in European Application No. 19875460.8.

International Search Report and Written Opinion in corresponding International application No. PCT/US2018/025971 on Jul. 10, 2018.

International Search Report and Written Opinion in corresponding International application No. PCT/US2018/026118 on Jun. 15, 2018.

Toyama et al. Mitral annular motion in patients after transcatheler MitraClip and mitral valve surgery; Echocardiography 2017; 34: 334-339.

Boudjemline Y, Agnoletti G, Bonnel D, et al. Steps toward the percutaneous replacement of atrioventricular valves an experimental study. Journal of the American College of Cardiology 2005; 46:360-5.

Bai Y, Chen HY, Zang GJ, et al. Percutaneous establishment of tricuspid regurgitation: an experimental model for transcatheler tricuspid valve replacement. Chinese medical journal 2010; 123:806-9.

Laule M, Stangl V, Sanad W, Lembcke A, Baumann G, Stangl K. Percutaneous transfemoral management of severe secondary tricuspid regurgitation with Edwards Sapien XT bioprosthesis: first-in-man experience. Journal of the American College of Cardiology 2013; 61:1929-31.

Lauten A, Doenst T, Hamadanchi A, Franz M, Figulla HR. Percutaneous bicaval valve implantation for transcatheler treatment of tricuspid regurgitation: clinical observations and 12-month follow-up. Circulation Cardiovascular Interventions 2014; 7:268-72.

Lauten A, Ferrari M, Hekmal K, et al. Heterotopic transcatheler tricuspid valve implantation: first-in-man application of a novel approach to tricuspid regurgitation. European heart journal 2011; 32:1207-13.

Lauten A, Figulla HR, Unbehaun A, et al. Interventional Treatment of Severe Tricuspid Regurgitation: Early Clinical Experience in a Multicenter, Observational, First-in-Man Study. Circulation Cardiovascular interventions 2018; 11: e006061.

Lauten A, Figulla HR, Willich C, et al. Percutaneous caval stent valve implantation: investigation of an interventional approach for treatment of tricuspid regurgitation. European heart journal 2010; 31:1274-81.

Lauten A, Laube A, Schubert H, et al. Transcatheter treatment of tricuspid regurgitation by caval valve implantation—experimental evaluation of decellularized tissue valves in central venous position. Catheterization and cardiovascular interventions : official journal of the Society for Cardiac Angiography & Interventions 2014.

Figulla HR, Kiss K, Lauten A. Transcatheter interventions for tricuspid regurgitation—heterotopic technology: TricValve. EuroIntervention : journal of EuroPCR in collaboration with the Working Group on Interventional Cardiology of the European Society of Cardiology 2016; 12:Y116-8.

Barbanti M, Ye J, Pasupati S, El-Gamel A, Webb JG. The Helie transcatheter aortic dock for patients with aortic regurgitation. EuroIntervention : journal of EuroPCR in collaboration with the Working Group on Interventional Cardiology of the European Society of Cardiology 2013; 9 Suppl:S91-4.

Hahn RT, Meduri CU, Davidson CJ, et al. Early Feasibility Study of a Transcatheter Tricuspid Valve Annuloplasty: SCOUT Trial 30-Day Results. Journal of the American College of Cardiology 2017; 69:1795-806.

Rosser BA, Taramasso M, Maisano F. Transcatheter interventions for tricuspid regurgitation: TriCinch (4Tech). EuroIntervention : journal of EuroPCR in collaboration with the Working Group on Interventional Cardiology of the European Society of Cardiology 2016; 12:Y110-2.

Stephan van Bardeleben R, Tamm A, Emrich T, Munzel T, Schulz E. Percutaneous transvenous direct annuloplasty of a human tricuspid valve using the Valtech Cardioband. European heart journal 2017; 38:690.

Kuwata S, Taramasso M, Nietlispach F, Maisano F. Transcatheter tricuspid valve repair toward a surgical standard: first-in-man report of direct annuloplasty with a cardioband device to treat severe functional tricuspid regurgitation. European heart journal 2017.

Rogers J. Transcatheter TR solution 6: Millipede. Transcatheter Cardiovascular Therapeutics; 2017 Nov. 1, 2017; Denver, Colorado.

Parada-Campelo F, Perlman G, Philippon F, et al. First-in-Man Experience of a Novel Transcatheter Repair System for Treating Severe Tricuspid Regurgitation Journal of the American College of Cardiology 2015; 66:2475-83.

Nickenig G, Kowalski M, Hausleiter J, et al. Transcatheter Treatment of Severe Tricuspid Regurgitation With the Edge-to-Edge MitraClip Technique. Circulation 2017; 135:1802-14.

Cao P. Catheter-Based Tricuspid Valve Replacement Via Right Atrium: An Animal Experimental Study. Transcatheter Cardiovascular Therapeutics; 2017; Denver, Colorado.

(56) References Cited

OTHER PUBLICATIONS

Navia JL, Kapadia S, Elgharably H, et al. First-in-Human Implantations of the NaviGate Bioprosthesis in a Severely Dilated Tricuspid Annulus and in a Failed Tricuspid Annuloplasty Ring. Circulation Cardiovascular interventions 2017; 10.

Regueiro, et al. Transcatheter Mitral Valve Replacement: Insights From Early Clinical Experience and Future challenges; JACC vol. 69, No. 17, 2017; May 2, 2017: 2175-92.

Non-Final Office Action received for U.S. Appl. No. 15/943,792 dated Jan. 8, 2020, 50 pages.

Non-Final Office Action received for U.S. Appl. No. 15/943,971 dated Jan. 8, 2020, 49 pages.

International Search Report and Written Opinion issued in corresponding International Application No. PCT/US2019/057145 on Dec. 31, 2019.

International Preliminary Report on Patentability received for PCT Application Serial No. PCT/US2018/025971 dated Oct. 17, 2019, 9 pages.

International Preliminary Report on Patentability received for PCT Application Serial No. PCT/US2018/026118 dated Oct. 17, 2019, 11 pages.

European Communication pursuant to Article 94(3) EPC mailed Jun. 27, 2024, in European Application No. 19 825 443.5.

\* cited by examiner

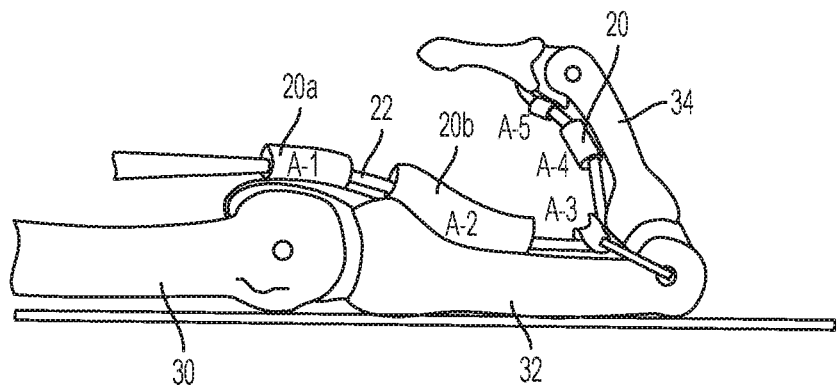
FIG. 1
PRIOR ART
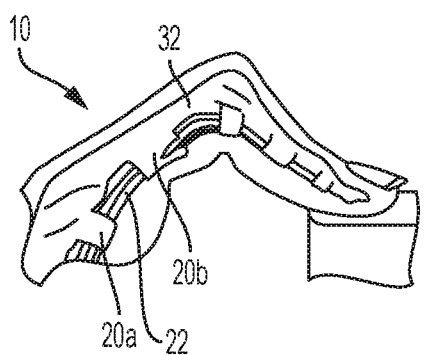 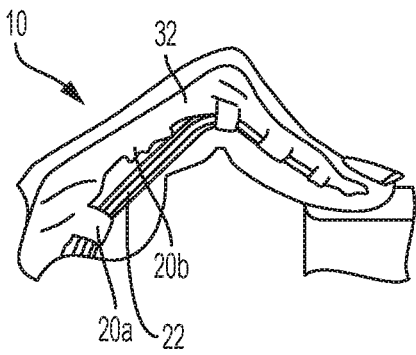
FIG. 2
PRIOR ART
FIG. 3
PRIOR ART
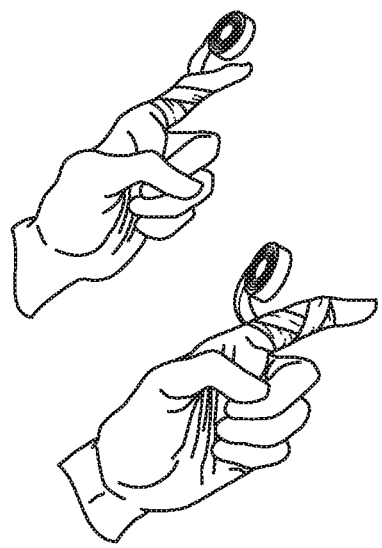
FIG. 4
PRIOR ART

BRACE FOR PREVENTING FINGER INJURIES

FIELD OF THE INVENTION

The present invention relates generally to rock-climbing gear, and more particularly to a finger-wearable brace for supporting the fingers during rock-climbing activities.

BACKGROUND

Rock climbing is a sport involving ascending rock cliffs using the climber's hands and feet to engage a rock face. The climber's hands are used to grip, hold and cling to the rock. For example, in face climbing, the climber primarily uses the fingertips and the palm of the hand to grasp features on the surface of a rock face. To be a successful in the sport, the rock climber's fingers must be strong and able to grip small ledges of rock formations while supporting the climber's body weight.

As well-known in the field of human anatomy and as shown in FIG. 1, fingers of a human's hand are manipulated when muscles in the forearm are flexed to manipulate flexor tendons. In a typical human hand, each finger has annular pulley ligaments 20 A-1-A-5 (and cruciate ligaments) that hold the finger's flexor tendon 22 close to the bones, e.g. the proximal phalanx 32 and middle phalanx 34, of the fingers to assist in providing mechanical leverage during flexion of the finger. The annular pulley ligaments 20 function as guiding sheathes to hold a corresponding tendon 22 in place in proximity to an associated phalanx as a finger is flexed, as will be appreciated from FIG. 1.

As shown in FIG. 2, a problem commonly occurs when one or more fingers 10 form a sharp angle, e.g., 90 degrees or less at the proximal interdigital join between the proximal and middle phalanxes—known as "crimping"—when grabbing a small, sometimes sharp hold, especially when the thumb is placed over the fingers ("full crimp"). Referring now to FIGS. 2 and 3, in such a hand position, a flexor tendon 22 in the proximal phalanx 32 (1st section of the finger) can be forced outwards, separating from the associated phalanx, and be caused to rupture an annular pulley ligament which the tendon normally passes (e.g., the A-2 annular pulley ligament 20b). This causes a serious and painful injury, sometimes referred to as a "bowstringing" injury, which results from separation of the flexor tendon 22 from the associated phalanx sufficient to tear an annular pulley ligament. Such a bowstring injury may require months of recovery time, which is typically time that a competitive athlete does not want to lose to an injury. FIG. 2 shows a bowstringing injury resulting from partial tearing of the A-2 annular pulley ligament 20b by the flexor tendon 22 due to excessive separation, sufficient to tear the pulley ligament, from the proximal phalanx 32. Fig. shows a bowstringing injury resulting from a full tear of the A-2 annular pulley ligament 20b by the flexor tendon 22 due to excessive separation from the proximal phalanx 32.

A conventional prior art approach for attempting to avoid such an injury involves applying flexible adhesive sports tape over the skin of the proximal phalanx, often in overlapping turns forming an H shape, as shown in FIG. 4. However, this applies relatively loose pressure to the finger, tendon and/or annular pulley ligament that provides ineffective and temporary support as the tape stretches, or becomes damaged or worn during climbing activities. Further, the tape is not reusable and must be discarded after a single rock climbing session.

Climbers gloves are known to protect the fingers and/or hand during climbing activities. Many such gloves are fingerless, like that disclosed in U.S. Pat. No. 5,079,776, to allow for direct contact between the rock features and the skin of the fingers. However, such gloves to not provide adequate support to the fingers and tendons of the fingers to avoid crimping and other injuries.

Accordingly, it remains desirable to provide a device for supporting the fingers to avoid crimping-related and other injuries to the fingers of a human hand.

SUMMARY

Provided herein are braces for preventing injuries to annular pulley ligaments of human hands. In accordance with one embodiment of the present invention, the brace comprises: a proximal band dimensioned to be worn on a proximal phalanx portion of a finger of a human hand in a position overlying an annular pulley ligament of the proximal phalanx; a distal band dimensioned to be worn on a middle phalanx portion of the finger; and a coupling attached to each of the proximal band and the distal band, the coupling permitting movement of the proximal band relative to the distal band when the brace is worn on the proximal and middle phalanx portions, respectively, of the finger, the coupling biasing the proximal band away from the distal band to promote retention of the proximal band in the position overlying the annular pulley ligament of the proximal phalanx.

In accordance with another embodiment, the brace comprises: a proximal band dimensioned to receive a proximal phalanx portion of a finger of a human hand, and to brace the finger's flexor tendon against separation from the proximal phalanx sufficient to cause tearing of an annular pulley ligament of the proximal phalanx; a distal band dimensioned to receive a middle phalanx portion of the finger; and a coupling attached to each of the proximal band and the distal band, the coupling limiting movement of the middle phalanx relative to the proximal phalanx to a predetermined range of motion for avoiding tearing of the annular pulley ligament when the proximal and distal bands are worn on the proximal and middle phalanx portions, respectively, of the finger.

In accordance with another embodiment, the brace comprises: a proximal band dimensioned to receive a proximal phalanx portion of a finger of a human hand, and to brace the finger's flexor tendon against separation from the proximal phalanx sufficient to tear an annular pulley ligament extending along the proximal phalanx portion; a distal band dimensioned to receive a middle phalanx portion of the finger of the human hand, and to brace the finger's flexor tendon against separation from the middle phalanx sufficient to tear a respective annular pulley ligament extending along the middle phalanx portion; and a coupling pivotably attached to each of the proximal band and the distal band, the coupling being operable to limit relative movement of the proximal and distal bands, when worn on the proximal and middle phalanx portions of the finger, to positions in which the proximal and middle phalanx portions form an angle therebetween greater than about 100 degrees, the coupling comprising: a first strut attached each of the proximal band and the distal band; and a second strut attached each of the proximal band and the distal band; wherein each of the struts comprises a piston movable between a retracted position and an extended position, the piston being biased towards the extended position by pressurized gas contained within the strut.

BRIEF DESCRIPTION OF THE FIGURES

FIG. 1 is a diagrammatic side view of exemplary bones, tendon and ligaments of a finger of a human hand, as known in the prior art;

FIG. 2 is a side view of an exemplary finger in an exemplary crimp position, showing exemplary partial tearing of the A-2 pulley ligament, as known in the prior art;

FIG. 3 is a side view of an exemplary finger in an exemplary crimp position, showing a full tear of the A-2 pulley ligament, as known in the prior art;

FIG. 4 is a perspective view of a finger shown wrapped in flexible adhesive tape in accordance with a common prior art approach to avoiding a pulley ligament injury;

DETAILED DESCRIPTION

The present invention can be understood more readily by reference to the following detailed description, examples, and claims. Before the present system, devices, and/or methods are disclosed and described, it is to be understood that this invention is not limited to the specific systems, devices, and/or methods disclosed unless otherwise specified, as such can, of course, vary. It is also to be understood that the terminology used herein is for the purpose of describing particular aspects only and is not intended to be limiting.

The following description is provided as an enabling teaching of the present invention. Those skilled in the relevant art will recognize that many changes can be made to the aspects described, while still obtaining the beneficial results of the present invention. It will also be apparent that some of the desired benefits of the present invention can be obtained by selecting some of the features of the present invention without utilizing other features. Accordingly, those of ordinary skill in the art will recognize that many modifications and adaptations to the present invention are possible and can even be desirable in certain circumstances and are a part of the present invention. Thus, the following description is provided as illustrative of the principles of the present invention and not in limitation thereof.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. Further, it should be understood that each range expressed includes all subsets of ranges within the range expressed.

Figure 5:
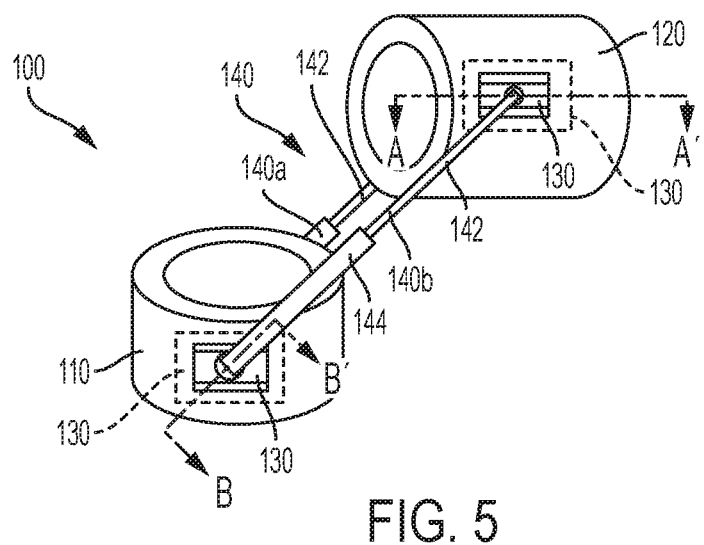
FIG. 5 is a perspective view of an exemplary brace for preventing finger injuries in accordance with a first exemplary embodiment of the present invention.

The present invention provides a brace device for supporting the fingers, and particularly the flexor tendons and annular pulley ligaments of the fingers, to avoid crimping-related and other injuries to the fingers of a human hand. FIG. 5 shows an exemplary brace 100 in accordance with a first exemplary embodiment of the present invention. Referring now to FIGS. 5 and 7, the brace 100 includes a proximal band 110 dimensioned to be worn on a proximal phalanx portion 32 of a finger 10 of a human hand in a position overlying an annular pulley ligament (e.g., the A-2 ligament shown in FIG. 1) of the proximal phalanx 32. The brace 100 further includes a distal band 120 dimensioned to be worn on a middle phalanx portion 34 of the finger 10.

The bands may be constructed as closed-loop rings having circular or non-circular cross sections as shown in FIG. 5, or in open-loop shapes for at least partially encircling a finger.

In the embodiment shown in FIG. 5, each band 110, 120 is constructed as a closed loop of an elastic material, such as a natural or synthetic rubber material, to accommodate fingers of a range of sizes due to the elasticity of the band itself. Suitable materials are relatively resistant to abrasion and other damage of the sort encountered during rock climbing activities, and provide sufficient elasticity to accommodate a range of finger sizes while avoiding elasticity insufficient to prevent tearing of the annular pulley ligaments during use. Preferably, the material and/or size of the bands are selected to fit closely with the finger with little or no gap between the internal surface of the band and the skin of the finger, and in some embodiments to encircle and compress the bodily tissue of the finger.

Each band 110, 120 is constructed so as to brace the finger's flexor tendon against separation from the proximal phalanx sufficient to cause tearing of an annular pulley ligament of the proximal phalanx, or otherwise fit snugly on the relevant portion of the finger. By way of example, bands having internal diameters in the range of about 0.375 inches to about 1.0 inches may be suitable for this purpose, though bands of any suitable size may be used. By way of example, limiting separation of the flexor tendon from the proximal phalanx to less than about 0.25 inches, and preferably less than about 0.125 inches, from the proximal phalanx can be sufficient to prevent tearing of the annular pulley ligament of the proximal phalanx.

Preferably, each of the proximal and distal bands 110, 120 has a respective length less than a length of the respective proximal and middle phalanx so as to rest on a respective phalanx without interfering with operation of any of the metacarpophalangeal, proximal interdigital or distal interdigital joints. By way of example, band lengths in the range about 1 cm to about 4 cm are suitable for this purpose, though bands of any suitable length may be used. Further, a wall of each of the proximal and distal bands 110, 120 has a respective thickness, which may be uniform or non-uniform, that is preferably small enough so as not to interfere with adjacent fingers. By way of example, band thicknesses in the range of about 0.25 cm to about 1.0 cm are suitable for this purpose, though bands of any suitable thickness may be used.

Referring again to FIG. 5, the brace 100 further includes a coupling 140 attached to each of the proximal band 110 and the distal band 120. The coupling 140 limits movement of the proximal band 110 relative to the distal band 120. Further, the coupling 140 limits movement of the middle phalanx 34 relative to the proximal phalanx 32 to a predetermined range of motion for avoiding tearing of the annular pulley ligament when the proximal and distal bands are worn on the proximal and middle phalanx portions, respectively, of the finger. Because it has been determined that annular pulley injuries more commonly occur when the finger is in a tight crimp position in which the proximal and middle phalanxes form an angle therebetween (at the proximal interdigital joint) of about 90 degrees or less, in certain embodiments, the brace limits relative movement of the proximal and distal bands, when worn on the proximal and middle phalanx portions of the finger, to positions in which the proximal and middle phalanx portions form an angle therebetween greater than about 90 degrees, and preferably, greater than about 100 degrees.

Preferably, the coupling 140 is operable to be compressible in length, and to resile so as to bias the proximal band away from the distal band to promote retention of the proximal band in a preferred position in which it overlies the A-2 annular pulley ligament of the proximal phalanx when the proximal and distal bands 110, 120 are worn on the proximal and middle phalanxes of the finger.

In certain embodiments, the coupling 140 comprises a first coupling member 140a attached to each of the proximal band 110 and the distal band 120, and a second coupling member 140b attached to each of the proximal band 110 and the distal band 120, as shown in FIG. 5.

Figure 6A:
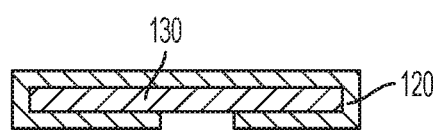
FIG. 6A is a cross-sectional view of a ring of the brace of FIG. 5, taken along line A-A' of FIG. 5.

In embodiments in which the bands are constructed of rubber or other elastic material, the band itself may not provide sufficient structuring rigidity for a stable mechanical coupling. In such embodiments, each band may comprise a ring of elastic material supporting a pair of rigid coupling support members 130, e.g., disposed at diametrically opposed positions (e.g., 180 degrees apart) about a periphery of the ring. By way of example, the rigid coupling support members 130 may be adhered to or otherwise mounted on an external surface of a corresponding band. In other embodiments, the ring of elastic material is molded around its respective pair of rigid coupling support members, such that the rigid coupling support member is embedded within material of the band, as will be appreciated from FIGS. 5 and 6A. Preferably, the rigid coupling support member 130 does not span an entire periphery of the band, so that there are portions of the elastic band between the rigid coupling support members that are more susceptible to expanding to accommodate a range of finger sizes, and/or movement of the finger during rock climbing activities, as will be appreciated from FIG. 5. For example, each rigid coupling support may span no more than about ⅛ to about ⅓ of the periphery of the band.

The material of the rigid coupling support member 130 is more rigid than the material of the elastic band, and thus provides an attachment point for forming a more stable mechanical coupling. Each of the first and second coupling members 140a, 140b is attached to a respective rigid coupling support member 130 of each of the proximal band 110 and the distal band 120 as shown in FIG. 5.

Figure 6B:
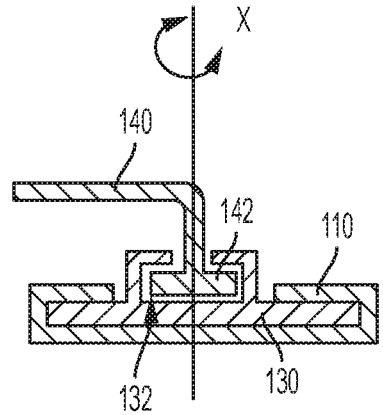
FIG. 6B is a cross-sectional view of a ring of the brace of FIG. 5, taken along line B-B' of FIG. 5.

In certain embodiments, as shown in FIGS. 5 and 6B, each coupling member 140a, 140b is pivotably attached to each of the respective rigid coupling support members 130, e.g., via a pivot pin or joint, a ball-and-socket joint, a stud, etc. Any suitable structure may be used for this purpose. In the exemplary embodiment shown in FIGS. 5 and 6B, each coupling member 140a, 140b is pivotably attached to each of the respective rigid coupling support members 130 by a joint permitting relative rotation about a single axis X, as best shown in FIG. 6B. In this exemplary embodiment, each rigid coupling support member 130 defines a cylindrical cavity 132 for receiving a complementary cylindrical lug 142 of a respective coupling member 140, such that the lug 142 rides within the cavity 132 with close tolerances so as to permit rotation about a single axis.

Figures 7A, 7B:
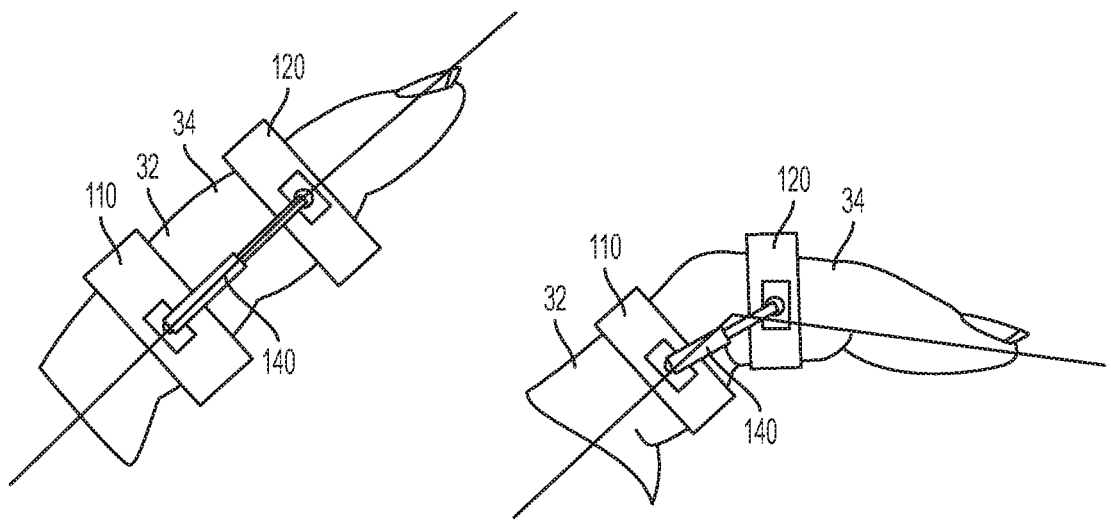
FIG. 7A is a side view of the brace of FIG. 5, showing for illustrative purposes the brace as worn on a finger in which the proximal interdigital joint is in an unflexed state.
FIG. 7B is a side view of the brace of FIG. 5, showing for illustrative purposes the brace as worn on a finger in which the proximal interdigital joint is in a flexed state.

In the exemplary embodiment shown in FIG. 5, each of the first and second coupling members comprises a strut 140a, 140b comprising a piston 142 movable between a retracted position and an extended position. The piston 142 of the strut rides within a gas-pressurized cylinder 144. Accordingly, the strut is biased towards the extended position by pressurized gas contained within the strut. The biasing is caused by releasing of stored energy created by compressed gas within the cylinder, causing the piston to extend. This results in biasing of the proximal band away from the distal band that promotes retention of the proximal band in the preferred position overlying the annular pulley ligament of the proximal phalanx when the proximal and distal bands 110, 120 are worn on the proximal and middle phalanxes of the finger. FIG. 7A is a side view of the brace of FIG. 5, showing for illustrative purposes the brace as worn on a finger in which the proximal interdigital joint is in an unflexed state. In this position, the coupling/piston is in a relatively relaxed state, e.g., in its extended position.

Further, the struts are preferably configured so that they provide a mechanical stop limiting the relative movement of the proximal and distal bands, when worn on the proximal and middle phalanx portions of the human hand, to positions in which the proximal and middle phalanx portions form an angle therebetween (at the proximal interdigital joint) greater than about 100 degrees. A range of movement of the piston of about 0.75 inches or less, about 0.5 inches or less, or about 0.25 inches or less may be suitable for this purpose. This involves the piston 142 reaching its fully-retracted position (in which it interferes with an end of the cylinder 144 or another internal stop structure within the cylinder) when the proximal and middle phalanx portions form therebetween an angle of about 100 degrees. This prevents the finger from assuming a crimp position that is relatively more likely to cause an annular pully injury, namely, a position in which the proximal and middle phalanx portions form an angle therebetween of about 90 degrees of less. FIG. 7B is a side view of the brace of FIG. 5, showing for illustrative purposes the brace as worn on a finger in which the proximal interdigital joint is in a flexed state. In this example, the proximal and middle phalanx portions are forming therebetween an angle of about 100 degrees, and thus the piston 142 has "bottomed out" in that it has traveled within the cylinder 144 to a point at which it abuts internal structure of the cylinder acting as a mechanical stop, so that further travel of the piston within the cylinder 144 is not possible, and thus further flexion of the corresponding finger to positions in which annular pulley injuries are increasingly likely is not possible.

Figures 8, 9:
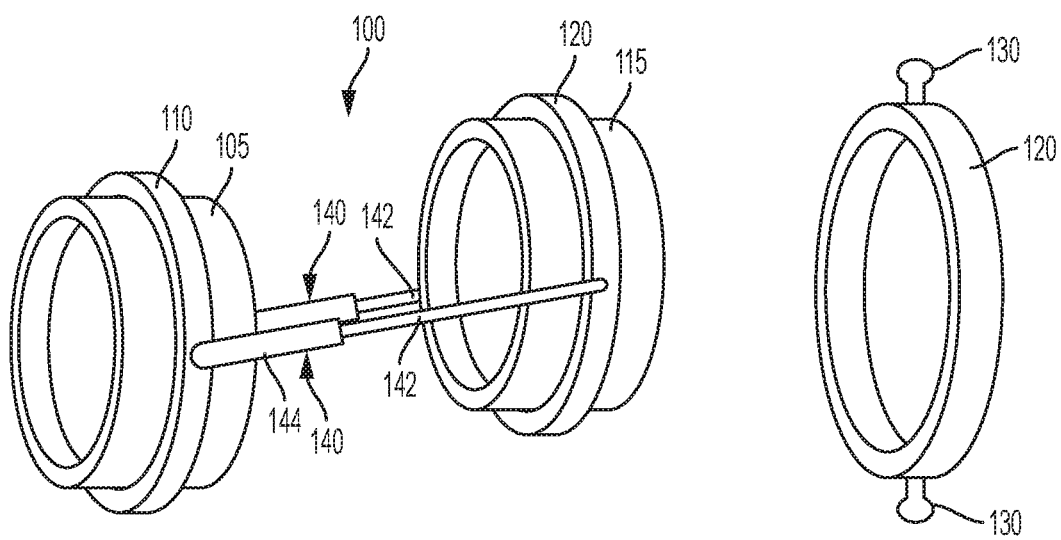
FIG. 8 is a perspective view of an exemplary brace for preventing finger injuries in accordance with a second exemplary embodiment of the present invention.
FIG. 9 is a perspective view of a band of the brace of FIG. 8.

FIG. 8 is a perspective view of an exemplary brace for preventing finger injuries in accordance with a second exemplary embodiment of the present invention. This embodiment is similar to that of FIG. 5 in many respects. However, in this embodiment, each band 110, 120 is constructed of an inelastic material, such as a steel, brass or another metal. In such embodiments, the bands may be constructed to provide a central opening sized for receipt of a finger of a common size. In such embodiments, bands of different sizes may be provided to accommodate fingers of a range of sizes. Alternatively, as shown in FIG. 8, a pliable liner of elastic material 105, 115, such as a silicone or relatively soft rubber, or a padding material, such as a foam rubber material, may be provided in the internal portion of the band, such that an inelastic band of a single size may accommodate a broader range of finger sizes due to pliability of the pliable liner 105, 115.

In embodiments in which the bands 110, 120 are constructed of metal or another inelastic material, each coupling member may be fixed directly to each band, e.g., by way of pivot pin or joint, a stud, a ball-and-socket joint, etc., because the band itself provides sufficient structural rigidity for a stable mechanical coupling. In the example of FIG. 8, each coupling member 150 defines a socket for mating to form a ball-and-socket joint with ball-type studs 130 that are fixedly attached to each ring in diametrically opposed positions, as shown in FIG. 9 with respect to exemplary band 120.

Figures 10A, 10B:
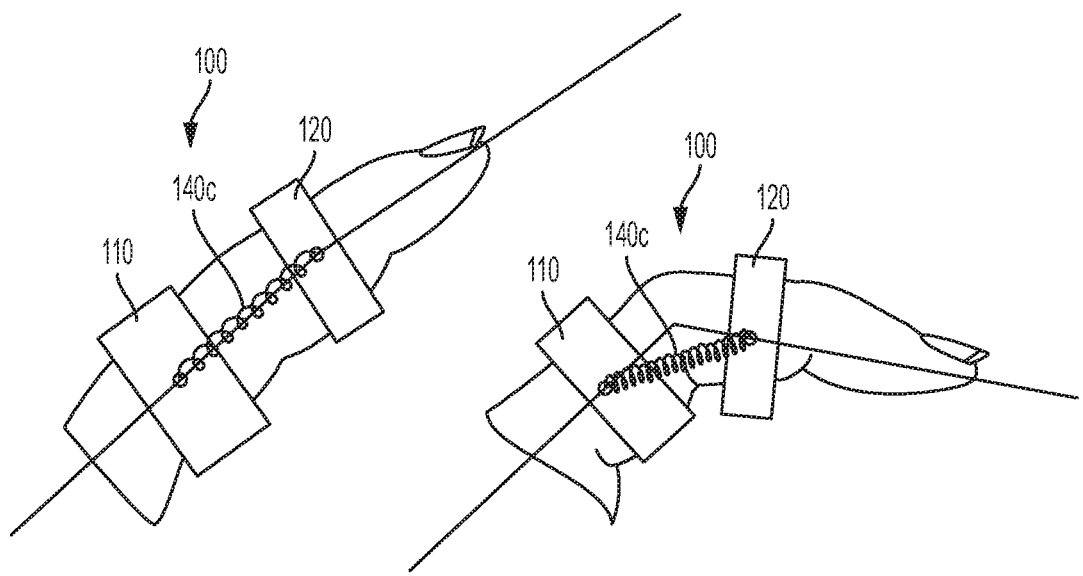
FIG. 10A is a side view of an exemplary brace for preventing finger injuries in accordance with a third exemplary embodiment of the present invention, showing for illustrative purposes the brace as worn on a finger in which the proximal interdigital joint is in an unflexed state.
FIG. 10B is a side view of the brace of FIG. 10A, showing for illustrative purposes the brace as worn on a finger in which the proximal interdigital joint is in a flexed state.

FIGS. 10A and 10B are side views of an exemplary brace 100 for preventing finger injuries in accordance with a third exemplary embodiment of the present invention. This embodiment is similar to that described above with reference to FIG. 5, but includes spring-type coupling members. Preferably, the spring-type coupling member is a compressible coil spring 140c, as shown in FIGS. 10A and 10B, and the brace is worn so that the springs 140c are in an uncompressed or only partially-compressed state when the proximal interdigital joint is in an unflexed state (i.e., when the proximal and middle phalanxes form a 180 degree angle therebetween as shown in FIG. 10A), and further is fully compressed, such that the coils of the spring abut one another, when the proximal and middle phalanxes form therebetween an angle of about 100 degrees, as shown in FIG. 10B. In this manner, the spring 140c provides a mechanical stop to limit the relative movement of the proximal and distal bands, when worn on the proximal and middle phalanx portions of the human hand, to positions in which the proximal and middle phalanx portions form an angle therebetween (at the proximal interdigital joint) greater than about 100 degrees. This prevents the finger from assuming a crimp position that is relatively more likely to cause an annular pulley injury, namely, a position in which the proximal and middle phalanx portions for an angle therebetween of about 90 degrees of less. In embodiments in which the coupling members are springs, the springs may be either pivotably attached, e.g. via pivot pin, joint or stud, or fixedly attached to each band 110, 120, as shown in the example of FIGS. 10A and 10B.

In use, the braces described herein can be worn on a climber's finger by inserting the finger (such as an index, middle, or ring finger) through the central openings of the bands 110, 120 until the distal band 120 is seated firmly over the middle phalanx 34, and the proximal band 110 is seated firmly around the proximal phalanx 32, preferably with the proximal band overlying the A-2 annular pulley ligament. From the climber's perspective, this may be achieved by positioning the proximal band close to the metacarpophalangeal joint, over the body of the proximal phalanx, close to its base portion (basis phalangis), where the A-2 annular pulley ligament is located. Optionally, the brace 100 may be worn on the finger so that the distal band also overlies the A-4 annular pulley ligament.

The brace 100 should be worn on the finger so that the coupling members extend along the sides of the finger, as shown in FIGS. 7A and 7B, so that the coupling members 140 do not interfere with the structure of the finger during flexion of the finger. If available, the climber may select a brace from a plurality of braces having different band sizes to ensure that the brace is well-matched in size to the climber's finger so that the bands seat snugly, and preferably compress, the bodily tissue around the phalanxes to facilitate in bracing the finger's flexor tendon against separation from the proximal phalanx sufficient to cause tearing of an annular pulley ligament of the proximal phalanx. Each band may be fixed in size and accommodate a narrow range of finger sizes. Alternatively, each band may include internal cushioning or padding to accommodate a broader range of finger sizes. Further, each band may be elastic, resilient, or otherwise expandable or adjustable to accommodate a broader range of finger sizes.

With the distal band 120 securely seated on the middle phalanx 34, the coupling members are biased toward their relaxed states, e.g. the extended position for the pistons 140a, 140b and the uncompressed state for the spring 140c. This tends to bias the proximal band 110 away from the distal band 120 to promote positioning and retention of the proximal band 110 over the A-2 annular pulley ligament of the finger.

Further, during rock climbing activities, the user may flex the finger to grasp rock faces, etc. During use and flexion, the biasing of the coupling member will resist movement of the proximal band 110 away from the preferred position over the A-2 annular pulley ligament of the finger. If the proximal band shifts position along the finger, the coupling member will operate to restore the distal band 120 to the preferred position over the A-2 annular pulley ligament. Such flexion of the finger at least partially compresses the piston or spring, which further promotes the coupling member's biasing of the proximal band toward the preferred position over the A-2 annular pulley ligament, as the coupling member operates to release energy stored in the form of compressed gas in the cylinder of the strut or compression of the spring, and resile towards a more relaxed state.

Further still, when the user flexes the finger to grasp rock faces, etc. the fingers might tend to assume a crimp position in which injury to the finger, e.g., due to bowstringing of the finger's flexor tendon and associated tearing of an annular pulley ligament, becomes more likely. In part, the proximal band 110 will resist and/or prevent such tearing of the A-2 pulley ligament because the proximal band 110 braces the finger's flexor tendon against separation from the proximal phalanx sufficient to cause tearing of an annular pulley ligament of the proximal phalanx. Similarly, the distal band 120 may resist and/or prevent tearing of the A-4 annularly pulley ligament because the distal band 120 braces the finger's flexor tending against separation from the middle phalanx sufficient to cause tearing of an annular pulley ligament and the middle phalanx. More particularly, the flexor tendon abuts the structure of the band, and is supported by the band, before the flexor tendon would separate sufficiently from the associated phalanx to tear the annular ligament pulley.

Still further, when the user flexes the finger to grasp rock faces, the fingers will be prevented from assuming a crimp position in which injury to the finger, e.g., due to bowstringing of the finger's flexor tendon and associated tearing of an annular pulley ligament, becomes more likely. More particularly, during flexion of the finger, the coupling members provide a mechanical stop limiting the relative movement of the proximal and distal bands, when worn on the proximal and middle phalanx portions of the human hand, to positions in which the proximal and middle phalanx portions form an angle therebetween greater than about 100 degrees, thereby avoiding positions of about 90 degrees of less in which bowstringing injuries are more likely. More specifically, during flexion of the finger, further flexion of the finger to undesirable flexion positions is prevented by the piston 142 of a strut-type coupling member 140a, 140b interfering with internal stop structure of the cylinder 144 as shown in FIG. 7B, or by the individual coils of a spring-type coupling member 140c abutting one another as shown in FIG. 10B.

Notably, the brace does not provide sufficient resistance to flexion of the finger that normal climbing activities are unduly impeded. Further, due to the durability and strength of the materials of the brace, and the structure of the brace, the brace will not loosen, stretch or become damaged to the point of decreased performance during a typical rock climbing session, and further the brace may be removed and reused during a subsequent climbing session.

Although several aspects of the invention have been disclosed in the foregoing specification, it is understood by those skilled in the art that many modifications and other aspects of the invention will come to mind to which the invention pertains, having the benefit of the teaching presented in the foregoing description and associated drawings. It is thus understood that the invention is not limited to the specific aspects disclosed hereinabove, and that many modifications and other aspects are intended to be included within the scope of the appended claims. Moreover, although specific terms are employed herein, as well as in the claims that follow, they are used only in a generic and descriptive sense, and not for the purposes of limiting the described invention.

What is claimed is:

1. A brace for preventing injuries to annular pulley ligaments of human hands, the brace comprising:
   a proximal band configured and dimensioned to be worn encircling a proximal phalanx portion of a finger of a human hand in a position overlying, abutting and supporting an annular pulley ligament of the proximal phalanx without interfering with flexion of a metacarpophalangeal and a proximal interdigital joint;
   a distal band dimensioned to be worn on a middle phalanx portion of the finger without interfering with flexion of the proximal interdigital joint and a distal interdigital joint; and
   a coupling consisting of a compressible coil spring non-movably attached to each of the proximal band and the distal band, the compressible coil spring permitting linear movement along an axis of elongation of the proximal and distal bands, the compressible coil spring being dimensioned and configured to (i) be in a relaxed state in which coils of the compressible coil spring are in a non-abutting relationship when the proximal and distal bands are separated by a distance corresponding to a distance between the proximal and distal bands when the brace is worn on the finger's proximal and middle phalanx portions, (ii) be compressed during flexion of the finger so that the compressed coil spring provides a biasing force that varies according to the degree of flexion of the finger for biasing the proximal band away from the distal band to promote retention of the proximal band in the position overlying the annular pulley ligament of the proximal phalanx during flexion of the finger, and (iii) be in a fully compressed state in which coils of the compressible coil spring are in an abutting relationship when axes of the proximal and distal bands are separated by a predetermined angle, to provide a mechanical stop against further flexion of the finger and an annular pulley ligament injury from a crimped position by limiting movement of the middle phalanx relative to the proximal phalanx to a predetermined range of motion for avoiding tearing of the annular pulley ligament due to separation of a flexor tendon of the finger from a respective phalanx portion.

2. The brace of claim 1, wherein each of the proximal band and the distal band comprises:
   a respective ring of elastic material supporting a pair of rigid coupling support members disposed at diametrically opposed positions about a periphery of the respective ring.

3. The brace of claim 2, wherein each ring of elastic material is molded around its respective pair of rigid coupling support members.

4. The brace of claim 3, wherein said compressible coil spring is attached to respective rigid coupling support members of each of the proximal band and the distal band; and wherein said brace further comprises
   a second compressible coil spring attached to respective rigid coupling support members of each of the proximal band and the distal band.

5. The brace of claim 4, wherein said second compressible coil spring is pivotably attached to each of the respective rigid coupling support members of the proximal and distal bands.

6. The brace of claim 4, wherein said second compressible coil spring is pivotably attached to each of the respective rigid coupling support members by a joint permitting relative rotation about a single axis.

7. The brace of claim 1, wherein each of the proximal and distal bands comprises a ring of elastic material.

8. The brace of claim 1, wherein the coils of the compressible coil spring are configured to be in an abutting relationship to serve as a mechanical stop against flexion of the finger when axes of the proximal and distal bands are separated by an angle of 90 degrees or less.

9. A brace for preventing injuries to annular pulley ligaments of human hands, the brace comprising:
   a proximal band configured to be worn encircling a proximal phalanx portion of a finger of a human hand in a position overlying and supporting an annular pulley ligament of the proximal phalanx;
   a distal band dimensioned to be worn on a middle phalanx portion of the finger; and
   a coupling consisting of a compressible coil spring having a pair of ends, each of said pair of ends being non-movably attached to a respective one of the proximal band and the distal band at a respective fixed location to prevent movement of each of said pair of ends relative to the respective one of the proximal band and the distal band, the coupling being dimensioned to be in a relaxed state when the proximal and distal bands are separated by a distance corresponding to a distance between the proximal and distal bands and permitting movement of the proximal band relative to the distal band by way of extension and retraction of the coupling, said coupling being configured to be compressed during flexion of the finger so that the compressed coupling provides a biasing force, along a line passing through the respective fixed locations in a direction misaligned with an axis of flexion of the finger during flexion of the finger when the brace is worn on the proximal and middle phalanx portions, respectively, of the finger.

10. The brace of claim 9, wherein each of the proximal band and the distal band comprises:
   a respective ring of elastic material supporting a pair of rigid coupling support members disposed at diametrically opposed positions about a periphery of the respective ring.

11. The brace of claim 10, wherein each ring of elastic material is molded around its respective pair of rigid coupling support members.

12. The brace of claim 11, wherein the coupling comprises:
   a first coupling member attached to respective rigid coupling support members of each of the proximal band and the distal band; and
   a second coupling member attached to respective rigid coupling support members of each of the proximal band and the distal band.

13. The brace of claim 12, wherein each of the first and second coupling members is pivotably attached to each of the respective rigid coupling support members of the proximal and distal bands.

14. The brace of claim 12, wherein each of the first and second coupling members is pivotably attached to each of the respective rigid coupling support members by a joint permitting relative rotation about a single axis.

15. The brace of claim 9, wherein each of the proximal and distal bands comprises a ring of elastic material.

16. The brace of claim 9, wherein the coupling is configured to limit movement of the middle phalanx relative to the proximal phalanx to a predetermined range of motion for avoiding tearing of the annular pulley ligament due to separation of a flexor tendon of the finger from a respective phalanx portion, when the proximal and distal bands are worn on the proximal and middle phalanx portions, respectively, of the finger.

17. A brace for preventing injuries to annular pulley ligaments of human hands, the brace comprising:
   a proximal band dimensioned to receive a proximal phalanx portion of a finger of a human hand without interfering with flexion of a metacarpophalangeal and a proximal interdigital joint, and to abut and brace a flexor tendon of the finger against separation from the proximal phalanx causing tearing of an annular pulley ligament of the proximal phalanx;
   a distal band dimensioned to receive a middle phalanx portion of the finger without interfering with flexion of the proximal interdigital joint and a distal interdigital joint; and
   a coupling consisting of a compressible coil spring having a first end non-movably attached in a first fixed location to the proximal band and a second end non-movably attached in a second fixed location to the distal band in a manner to resist linear movement of the first end toward the second end and to limit movement of the middle phalanx relative to the proximal phalanx to a predetermined range of motion for avoiding tearing of the annular pulley ligament when the proximal and distal bands are worn on the proximal and middle phalanx portions, respectively, of the finger, the coupling being operable to restore at least one of the proximal and distal bands to at least one preferred position on the finger, in an event of movement of said at least one of the proximal and distal bands along the finger during flexion and extension of the finger, by providing a variable biasing force that does not involve movement of the first end and the second end of the coupling relative to the proximal band and distal band, respectively.

18. The brace of claim 17, wherein the coupling comprises:
   a first coupling member attached to each of the proximal band and the distal band; and
   a second coupling member attached to each of the proximal band and the distal band.

19. The brace of claim 18, wherein each of the first and second coupling members comprises a compressible coil spring dimensioned to be in a relaxed state when the proximal and distal bands are separated by a distance corresponding to a distance between the proximal and distal bands when worn on the proximal and middle phalanx portions of the finger.

* * * * *